(12) United States Patent
Hashimoto et al.

(10) Patent No.: US 7,195,597 B2
(45) Date of Patent: Mar. 27, 2007

(54) PULSE WAVE MEASURING APPARATUS

(75) Inventors: Masao Hashimoto, Kyoto (JP); Kazunobu Itonaga, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 363 days.

(21) Appl. No.: 10/751,112

(22) Filed: Jan. 5, 2004

(65) Prior Publication Data

US 2004/0193060 A1     Sep. 30, 2004

(30) Foreign Application Priority Data

Jan. 10, 2003   (JP) .............................. 2003-004356

(51) Int. Cl.
*A61B 5/00* (2006.01)

(52) U.S. Cl. .................... 600/500; 600/485; 600/503

(58) Field of Classification Search .................... None
See application file for complete search history.

(56) References Cited

U.S. PATENT DOCUMENTS

| | | |
|---|---|---|
| 4,320,767 A | 3/1982 | Villa-Real |
| 5,240,007 A | 8/1993 | Pytel et al. |
| 5,271,405 A | 12/1993 | Boyer et al. |
| 6,132,383 A * | 10/2000 | Chesney et al. ............ 600/502 |

FOREIGN PATENT DOCUMENTS

| | | |
|---|---|---|
| EP | 0 649 629 A2 | 10/1994 |
| EP | 1 360 930 | 11/2003 |
| JP | 2-39702 U | 3/1990 |

OTHER PUBLICATIONS

European Search Report dated May 10, 2004.
European Search Report dated Aug. 4, 2004.

* cited by examiner

*Primary Examiner*—Robert L Nasser
*Assistant Examiner*—Karen E Toth
(74) *Attorney, Agent, or Firm*—Morrison & Foerster LLP

(57) ABSTRACT

Provided is a pulse wave measuring apparatus preventing breakage of a pressure sensing surface in the non-measurement stage. The pulse wave measuring apparatus includes: a housing and a pressure sensing section, wherein an opening is formed at the bottom surface of the housing, the pressure sensing section is mounted inside of the housing, the pressure sensing section moves freely upwardly and downwardly through the opening between a measuring position at which a pressure sensing surface is pressed to a human body to measure a pulse wave and a waiting position at which the pressure sensing section 20 is accommodated inside of the housing to be on standby and the housing has a slide cover protecting the pressure sensing surface in a state where the pressure sensing section is located at the waiting position.

2 Claims, 14 Drawing Sheets

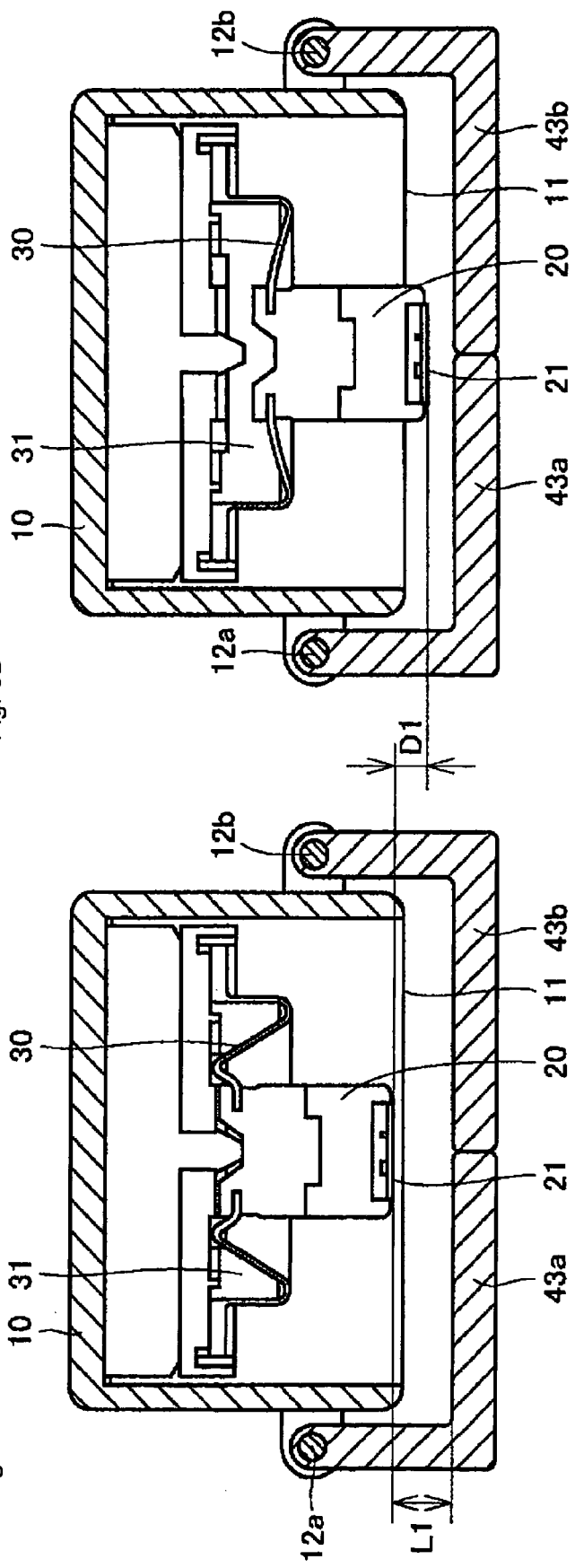

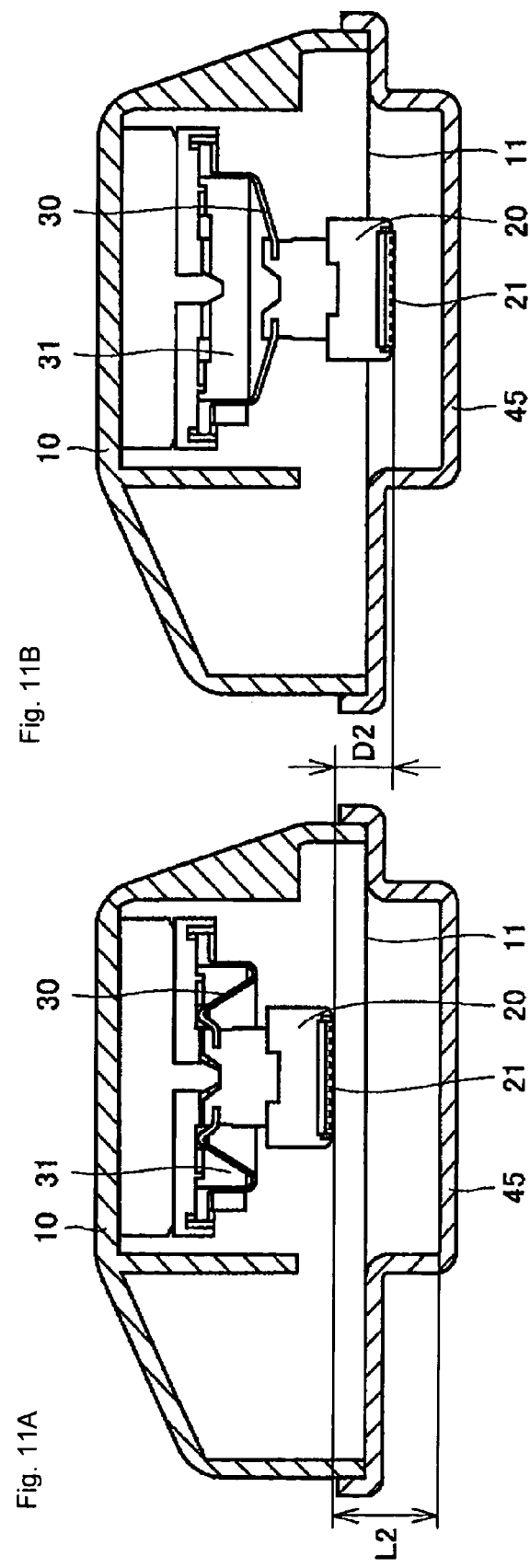

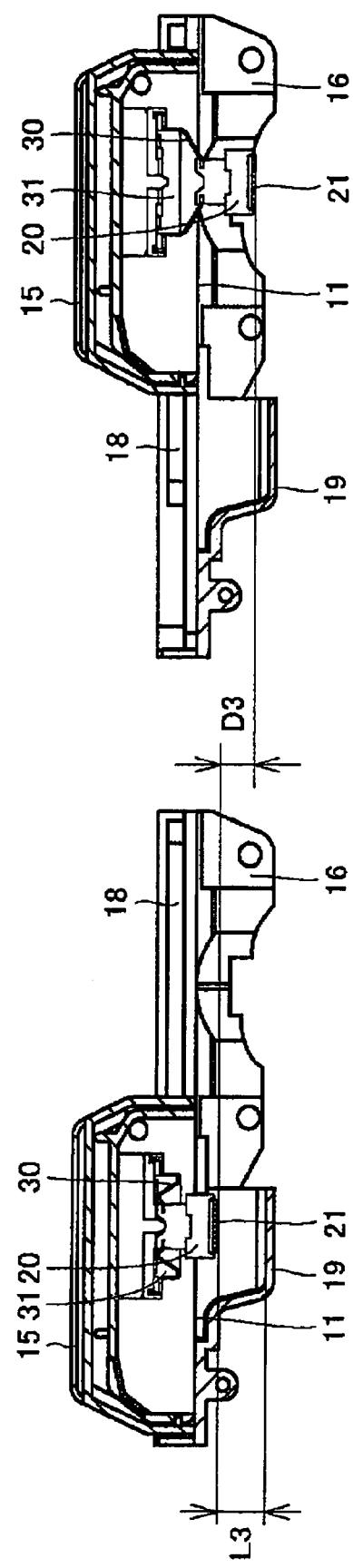

PULSE WAVE MEASURING APPARATUS

BACKGROUND OF THE INVENTION

1. Field of the Invention

The present invention relates to a pulse wave measuring apparatus, and more particularly, to a pressurization type pulse wave measuring apparatus measuring a pulse wave by pressing a pressure sensing section including a pressure sensing surface to a human body.

2. Description of the Prior Art

A pressurization type pressure measuring apparatus has been generally known in which a contact pressure between a measuring object and a pressure sensitive surface is measured by applying a pressure to the measuring object. A pulse wave measuring apparatus is an application of the pressurization type pressure measuring apparatus. A pulse wave measuring apparatus measures a wave pulse by pressing a substrate having a pressure sensing means to surface of a human body in measurement of the pulse wave generated in an artery located in shallow depth under the skin of a human body. It is very important to measure a pulse wave of a patient using such a pulse wave measuring apparatus in order to be familiar with a health condition of the patient.

In the pressurization type pulse wave measuring apparatus, it is general to use a semiconductor pressure detecting apparatus equipped with a strain gauge or a diaphragm as a pressure sensing means. In this case, a pressure sensing section is configured so that a pressure sensing means for sensing a pulse wave is located on a surface of a housing mounted to a human body. As a literature concerning this kind of a pressurization type pulse wave measuring apparatus, there can be named JP-A 63-275320 (patent literature 1).

In a pressurization type pulse wave measuring apparatus, there has remained a problem that a substrate on which a pressure sensing means is formed is broken with ease. Since, as a pressure sensing means, generally, a semiconductor pressure detecting apparatus is used, a semiconductor substrate is used as a substrate. A thickness of the semiconductor substrate is usually on the order in the range from 100 µm to 300 µm and in a case where a diaphragm is used as a pressure sensing element, a thickness of a diaphragm portion is very thin on the order in the range of from 4 µm to 10 µm. Hence, if an external force is imposed on a main surface of the semiconductor substrate, a case arises where cracking and chipping occurs on the semiconductor substrate. In a case where such cracking or chipping occurs, a pulse wave cannot be measured and a trouble occurs in the pulse wave measuring apparatus.

It is mainly in the non-measurement stage that an external force so strong that cracking and chipping occur on a semiconductor substrate is imposed on the semiconductor substrate. Since, in the measurement stage, a human body surface is pressed by a pressure sensing section with a proper pressure, there arises no worry for cracking and chipping to occur on a semiconductor substrate. In the non-measurement stage, however, the pressure sensing surface is aligned face to face with the plane including the edge of an opening provided in the housing; therefore, a user has had a chance to get in touch with the pressure sensing surface, thereby having resulted in breakage of the semiconductor substrate.

While a main surface of a semiconductor substrate is usually covered with a passivation film, such a protective film has no function to protect a pressure sensing surface sufficiently against an external force. Furthermore, a pulse wave measuring apparatus has been available in which a protective film such as a rubber film covers a pressure sensing surface, whereas a thickness thereof is suppressed to a value of the order in the range of from 50 µm to 400 µm because of reduction in detection accuracy in the measurement stage. Therefore, such protective films including a rubber film exert no sufficient protective function against an external force.

In a pressurization type pulse wave measuring apparatus, a pressure sensing section including a pressure sensing surface is mounted inside of a housing so as to be movable upwardly and downwardly. Accordingly, a mounting strength of the pressure sensing section to the housing is not so high as expected. Hence, there is also a fear that amounting portion of the pressure sensing section is broken if a great external force in a lateral direction acts on the pressure sensing section.

SUMMARY OF THE INVENTION

The invention has been made in order to solve the problems and it is accordingly an object of the invention to provide a pulse wave measuring apparatus in which a pressure sensing surface is prevented from being broken in the non-measurement stage.

It is another object of the invention to provide a pulse wave measuring apparatus having not only a pressure sensing surface but also all of a pressure sensing section protected in the non-measurement stage.

A pulse wave measuring apparatus based on the invention includes: a housing; and a pressure sensing section, wherein a pressure sensing surface of the pressure sensing section is pressed to a human body to measure a pulse wave. An opening is formed in the housing and the pressure sensing section is provided inside of the housing. The pressure sensing section moves freely upwardly and downwardly, through the opening formed in the housing, between a measuring position at which the pressure sensing surface is pressed to a human body to measure a pulse wave and a waiting position at which the pressure sensing section is accommodated inside of the housing to be on standby. The housing has a protective mechanism protecting the pressure sensing surface in a state where the pressure sensing section is located at the waiting position.

In such away, in a state where the pressure sensing section is at the waiting position, the pressure sensing surface can be protected in the non-measurement stage with certainty by providing a protective mechanism protecting the pressure sensing surface inside of the housing. With such a construction, it is possible to provide a pulse wave measuring apparatus preventing breakage of the pressure sensing surface in the non-measurement stage.

In the pulse measuring apparatus based on the invention described above, for example, it is preferable that the protective mechanism is constructed of a protective cover freely opening and closing the opening formed in the housing. With the protective cover freely opening and closing the opening in such a way provided to the housing, a construction can be possible in which the protective cover is opened in the measurement stage to conduct a rising and falling operation of the pressure sensitive section, while the protective cover closes the opening with the protective cover in the non-measurement stage not to thereby expose the pressure sensing surface. Hence, it is possible to surely protect the pressure sensing surface with the protective cover in the non-measurement stage. Furthermore, by closing the entire outermost area of the opening provided in the housing with the protective cover provided to the housing, it is possible to protect not only the pressure sensing surface but also the whole of pressure sensing section. Hence, it is possible to attain a pulse wave measuring apparatus hard to cause a trouble therein.

In a pulse wave measuring apparatus provided with the protective cover as described above, a construction is preferably adopted in which a distance between the protective cover and the pressure sensing surface in a state where the pressure sensing section is located at the waiting position is more than a moving distance of the pressure sensing section moving between the waiting position and the measuring position. With such a construction adopted, even in a case where a user wrongly operates the pulse wave measuring apparatus to start a measuring operation in a state where the opening is kept to be closed with the protective cover, it is avoided for the pressure sensing surface to be brought into contact with the protective cover. Hence, it is possible to protect the pressure sensing surface with more of certainty.

In the pulse wave measuring apparatus based on the invention described above, for example, the protective cover is preferably a slide cover mounted to the housing so as to be slidable on the housing. As an embodiment to provide the protective cover that is freely openable and closable to the housing, it is thought to adopt a slide cover as described above. With the slide cover as a protective cover adopted in such a way, it is possible to realize a protective mechanism excellent in operability with a simple and convenient construction.

In the pulse wave measuring apparatus based on the invention described above, for example, the protective cover is preferably a pivotable cover mounted to the housing in a freely pivotable manner. As an embodiment to provide the protective cover that is freely openable and closable to the housing, it is thought to adopt the pivotable cover as described above. With the pivotable cover as a protective cover adopted in such a way, it is possible to realize a protective mechanism excellent in handlability with a simple and convenient construction.

In the pulse wave measuring apparatus based on the invention, for example, the protective cover is preferably a cap mounted to the housing in a freely mountable and demountable manner. As an embodiment to provide the protective cover that is freely openable and closable to the housing, it is thought to adopt a cap. With the cap adopted as the protective cover, it is possible to realize the protective mechanism excellent in operability with a simple and convenient construction.

In the pulse wave measuring apparatus based on the invention, for example, the protective mechanism is preferably a rotation fixing means rotating the pressure sensing section half way and fixed so that the pressure surface is inclined to the plane including the edge of the opening at the waiting position. With the pressure sensing section mounted to the housing by the rotation fixing means in a freely rotatable manner in such a way, the pressure sensing surface is aligned face to face with the plane including the edge of the opening in the measurement stage, while in the non-measurement stage, the pressure sensing surface can be inclined to the plane including the edge of the opening, thereby enabling the pressure sensing surface to be protected with certainty. With such a construction adopted, it is possible to realize the protective mechanism excellent in operability with a simple and convenient construction.

In the pulse wave measuring apparatus based on the invention, for example, the housing is preferably constructed of a case body accommodating the pressure sensing section and a base body fixing the case body to a human body. In this case, the opening is provided in the case body and an insertion hole is necessary to be provided to the base body so that the pressure sensing section can move between the waiting position and the measuring position in a freely, upwardly and downwardly movable manner. Furthermore, the case body is preferably mounted to the base body so that the case body can slide between a first position at which the pressure sensing surface faces the insertion hole and a second position at which the pressure sensing surface does not face the insertion hole. In this case, the protective mechanism is preferably a protective cover section provided to the base body so that the protective mechanism faces the pressure sensing surface in a state where the case body is located at the second position.

With a construction in which the housing is divided into the case body and the base body adopted as described above, the pressure sensing section can be easily set at a position on a human body to be pressed with the pressure sensing section, that is a position on the surface of a human body right above an artery. In a case where the housing is divided in such a way, a construction can be adopted in which the case body slides on the base body. With such a construction, the pressure sensing section can be set at the first position, that is at a position at which a measuring operation can be started by sliding the case body after the pulse wave measuring apparatus is fixed at a measuring site of a patient. With such a construction adopted, it is possible to realize a pulse wave measuring apparatus excellent in handlability.

In a case with such a construction, the case body is located at the second position, that is at a position where a pulse wave cannot be measured in the non-measurement stage; therefore, a protective cover section is preferably provided to the base body so that the pressure sensing surface is not exposed at the second position. With the protective cover section provided to the base body, the pressure sensing surface can be protected with certainty in the non-measurement stage; thereby enabling a pulse wave measuring apparatus hard to cause a trouble therein to be provided.

In the pulse wave measuring apparatus in which the protective cover section is provided to the base body, as described above, a construction is preferable in which the pressure sensing section is located at the waiting position and a distance between the protective cover section and the pressure sensing surface in a state where the case body is located at the second position is more than a moving distance of the pressure sensing section moving between the waiting position and the measuring position. With such a construction adopted, even if a user wrongly operates the pulse wave measuring apparatus and starts a measuring operation in a state where the pressure sensing surface is kept to be protected by the protective cover section, it is avoided for the pressure sensing surface to be brought into contact with the protective cover section. Hence, it is possible to protect the pressure sensing surface with more certainty.

BRIEF DESCRIPTION OF THE DRAWINGS

FIG. 8A shows a schematic sectional view of an example modification of the pulse wave measuring apparatus in the second embodiment of the invention when a pressure sensing section is located at a waiting position and FIG. 8B shows a schematic sectional view of the example modification when the pressure sensing section is located at a measuring position.

FIG. 11A shows a schematic sectional view of the pulse wave measuring apparatus in the third embodiment of the invention when a pressure sensing section is located at a waiting position and FIG. 11B shows a schematic sectional view of the pulse wave measuring apparatus when the pressure sensing section is located at a measuring position.

FIG. 15A shows a view of a schematic sectional view of the pulse wave measuring apparatus in the fifth embodiment of the invention in a state where a pressure sensing section is located at a waiting position and FIG. 15B shows a view of a schematic sectional view of the pulse wave measuring apparatus in a state where the pressure sensing section is located at a measuring position.

DESCRIPTION OF THE PREFERRED EMBODIMENTS

First of all, description will be given of a structure of a pulse wave measuring apparatus to which the invention is applied. The pulse wave measuring apparatus described below is a so-called pressurization type pulse wave measuring apparatus used in a way such that a housing is fixed onto a patient so that an opening provided in the housing faces a measuring site of the patient and a pressure sensing section mounted inside of the housing is pressed through the opening onto a body surface of the patient to measure a pulse wave.

Figure 1:
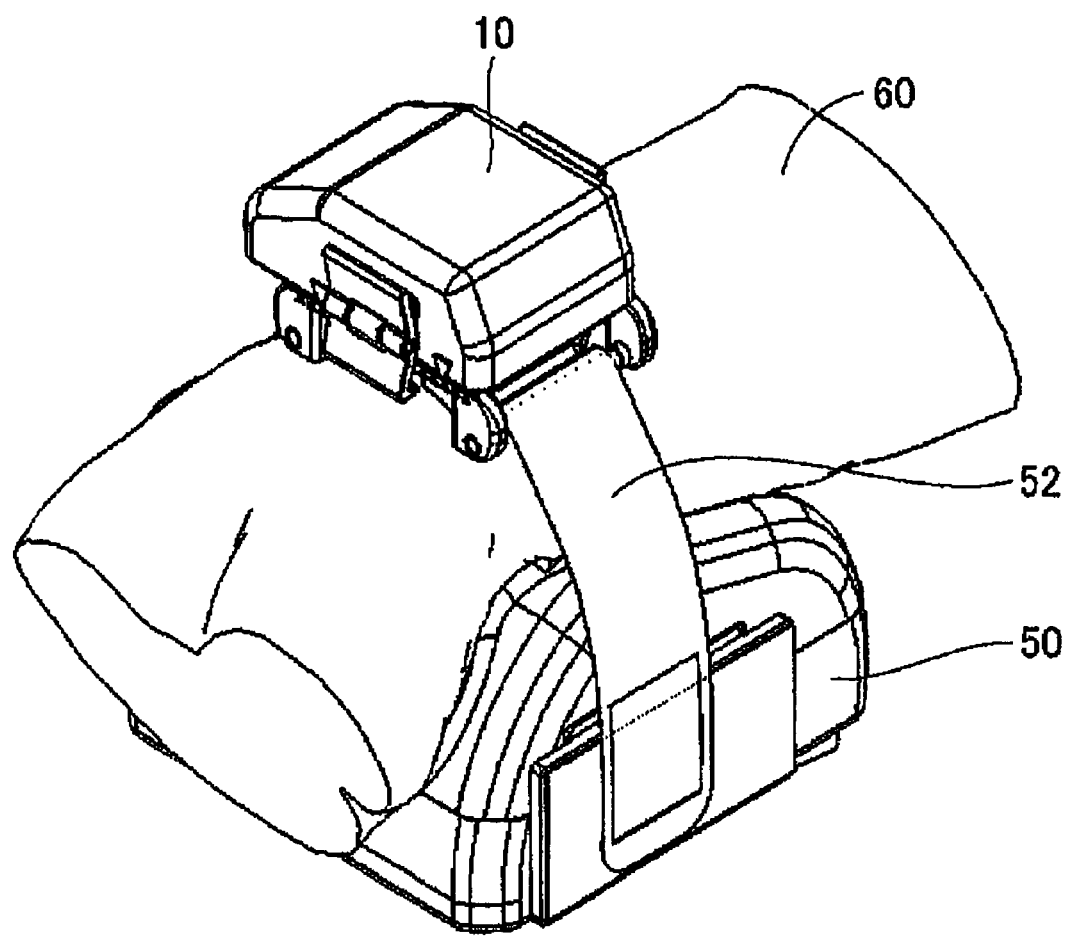
FIG. 1 shows a schematic perspective view of a pressurization type pulse wave measuring apparatus.
Figure 2A:
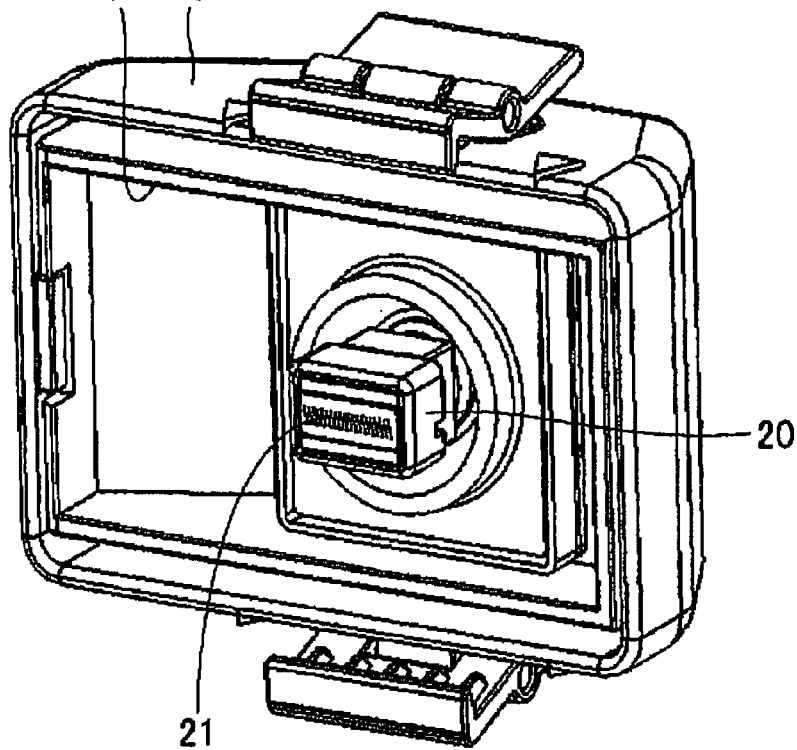
FIG. 2A shows a schematic perspective view of a housing of the pulse wave measuring apparatus shown in FIG. 1
Figure 2B:
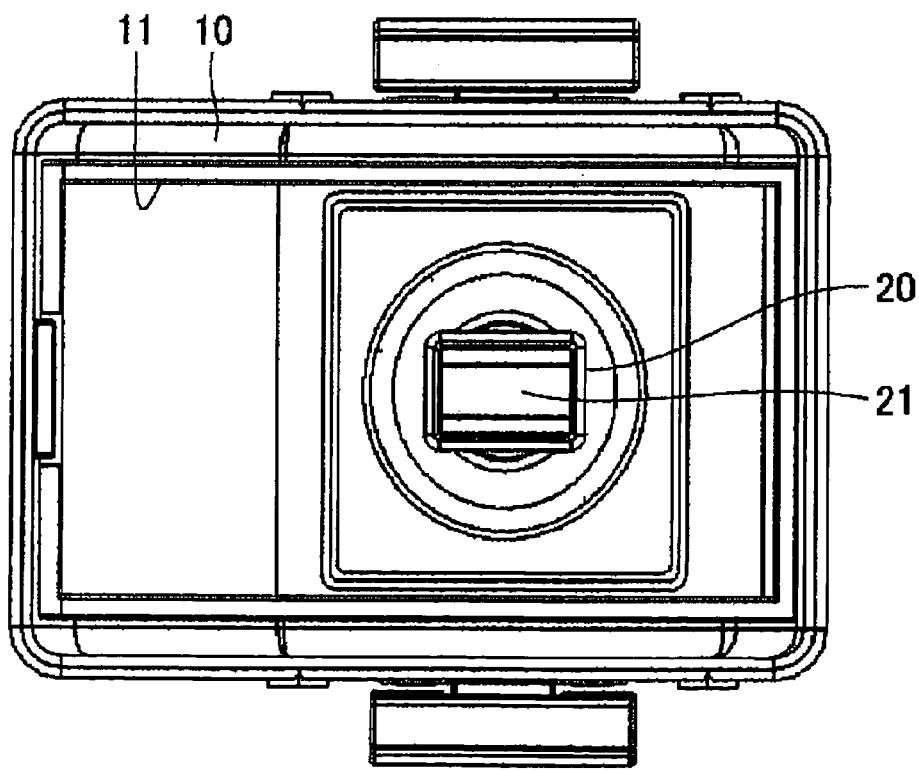
FIG. 2B shows a schematic bottom view of the housing.
Figure 3A:
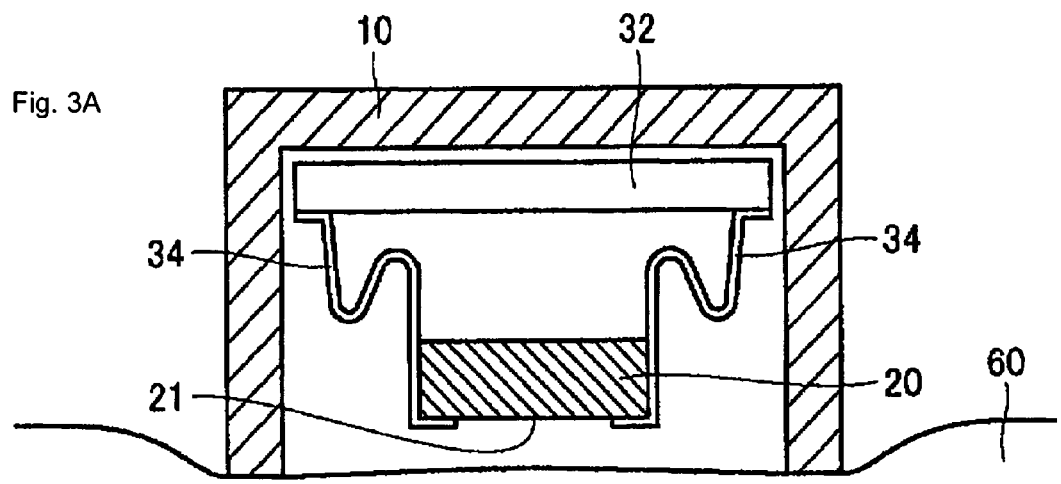
FIG. 3A shows a descriptive model view prior to measurement of a pressure mechanism of the pulse wave measuring apparatus shown in FIG. 1
Figure 3B:
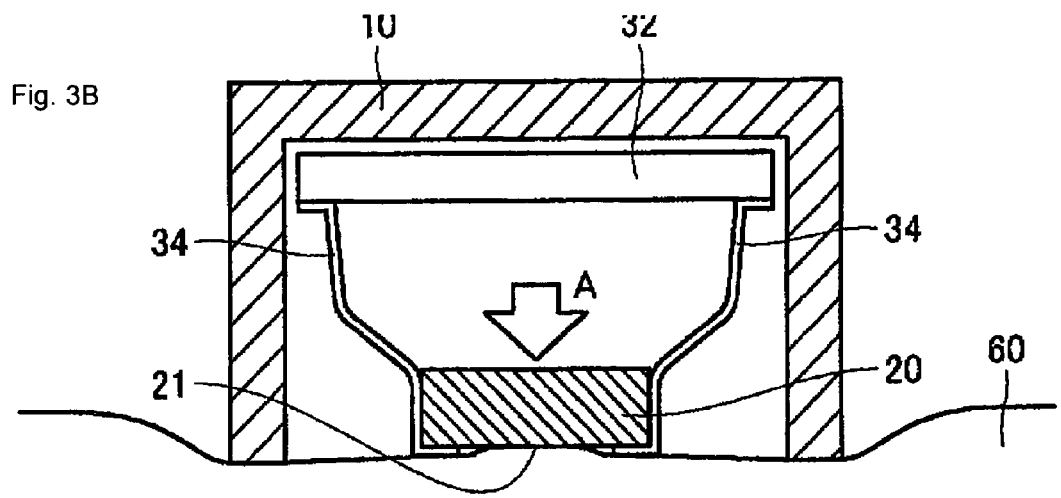
FIG. 3B shows a descriptive model view in the measurement stage thereof.

FIG. 1 is a schematic perspective view showing an overall structure of a pressurization type pulse wave measuring apparatus. FIG. 2A is a schematic perspective view of a housing of the pulse wave measuring apparatus shown in FIG. 1 and FIG. 2B is a schematic bottom view of the housing. FIG. 3A is a descriptive model view prior to measurement of a pressure mechanism of the pulse wave measuring apparatus shown in FIG. 1 and FIG. 3B is a descriptive model view in the measurement stage thereof.

Description will be given of the overall structure of the pressurization type of the pulse wave measuring apparatus with reference to FIGS. 1 and 2A and 2B. The pressurization type pulse wave measuring apparatus, as shown in FIG. 1, includes: a housing 10; a fixing support 50; and a belt 52. The fixing support 50 is a support for fixing a measuring site of part of the body 60 of a patient. In the pulse wave measuring apparatus shown in FIG. 1, a wrist of the patient is adopted as a measuring site where a pulse wave is measured. Hence, the fixing support 50 is shaped so as to enable the wrist to be fixed thereon.

The belt 52 is attached to a predetermined position of the fixing support 50. The housing 10 is attached to the belt 52. The housing 10 has a pressure sensing section 20 (see FIGS. 2A and 2B) inside thereof as described later. Hence, by winding the belt 52 around the wrist placed on the fixing support 50, the pressure sensing section 20 of the housing 10 is located above a measuring site of a patient.

The pressure sensing section 20 including a pressure sensing surface 21, as shown in FIGS. 2A and 2B, is provided inside of the housing 10 so as to be aligned face to face with the plane including the edge of an opening 11. The pressure sensing surface 21 corresponds to a main surface of a semiconductor substrate assembled in the pressure sensing section 20 and plural pressure sensing elements, which are pressure sensing means, are formed on the main surface of the semiconductor substrate. An air bag (not shown) for pressing the pressure sensing section 20 to a human body is attached on the top of the pressure sensing section 20. Note that the pressure sensing section 20 is supported so as to be freely movable upwardly and downwardly.

Description will be given of a pressurization mechanism of the pulse wave measuring apparatus shown in FIG. 1 with reference to FIGS. 3A and 3B. A circuit substrate 32 is provided inside of the housing 10 of the pulse wave measuring apparatus as shown in FIGS. 3A and 3B. A processing circuit processing signals outputted from the pressure sensing elements is formed on the circuit substrate 32. A flexible wiring 34 is used for transmission of signals outputted from the pressure sensing elements. One end of the flexible wiring 34 is connected electrically to the pressure sensing section 20 having pressure sensing elements and the other end thereof is connected electrically to the circuit substrate 32.

Prior to measurement, the pressure sensing section 20, as shown in FIG. 3A, is located at a position spaced from the body surface 60. This position at which the pressure sensing section 20 is accommodated inside of the housing 10 to wait is referred to as a waiting position. The air bag not shown is expanded in the measurement stage and thereby the pressure sensing section 20 moves, as shown in FIG. 3B, in a direction of an arrow mark A in the figure into a state where the pressure sensing surface 21 of the pressure sensing section 20 is pressed to the body surface 60. In this state, the pressure sensing elements detect a pulse wave generated in an artery located right under the skin of the body surface 60. This position at which the pressure sensing surface 21 is pressed to the body surface 60 to enable a pulse wave to be measured is referred to as a measuring position.

In the pressurization type pulse wave measuring apparatus having a construction described above, the pressure sensing section is mounted to the housing so that the pressure sensing section can move from the waiting position at which the pressure sensing section is accommodated inside of the housing to the measuring position at which the pressure sensing section is pressed to the body surface. Therefore, even in the non-measurement stage, the pressure sensing section is aligned face to face with the plane including the edge of the opening in an exposed state. In order to cope with such an inconvenience, the inventors prepare a cap that can be mounted to the pressure sensing section in a freely mountable and demountable manner and studied a protective mechanism protecting the pressure sensing surface by fitting the cap on the pressure sensing section in the non-measurement stage.

Description will be given of a pulse wave protective mechanism associated with the invention, which has been studied in the course till the inventors reaches the invention, with reference to the accompanying drawings ahead of description of embodiments of the invention.

Figure 4:
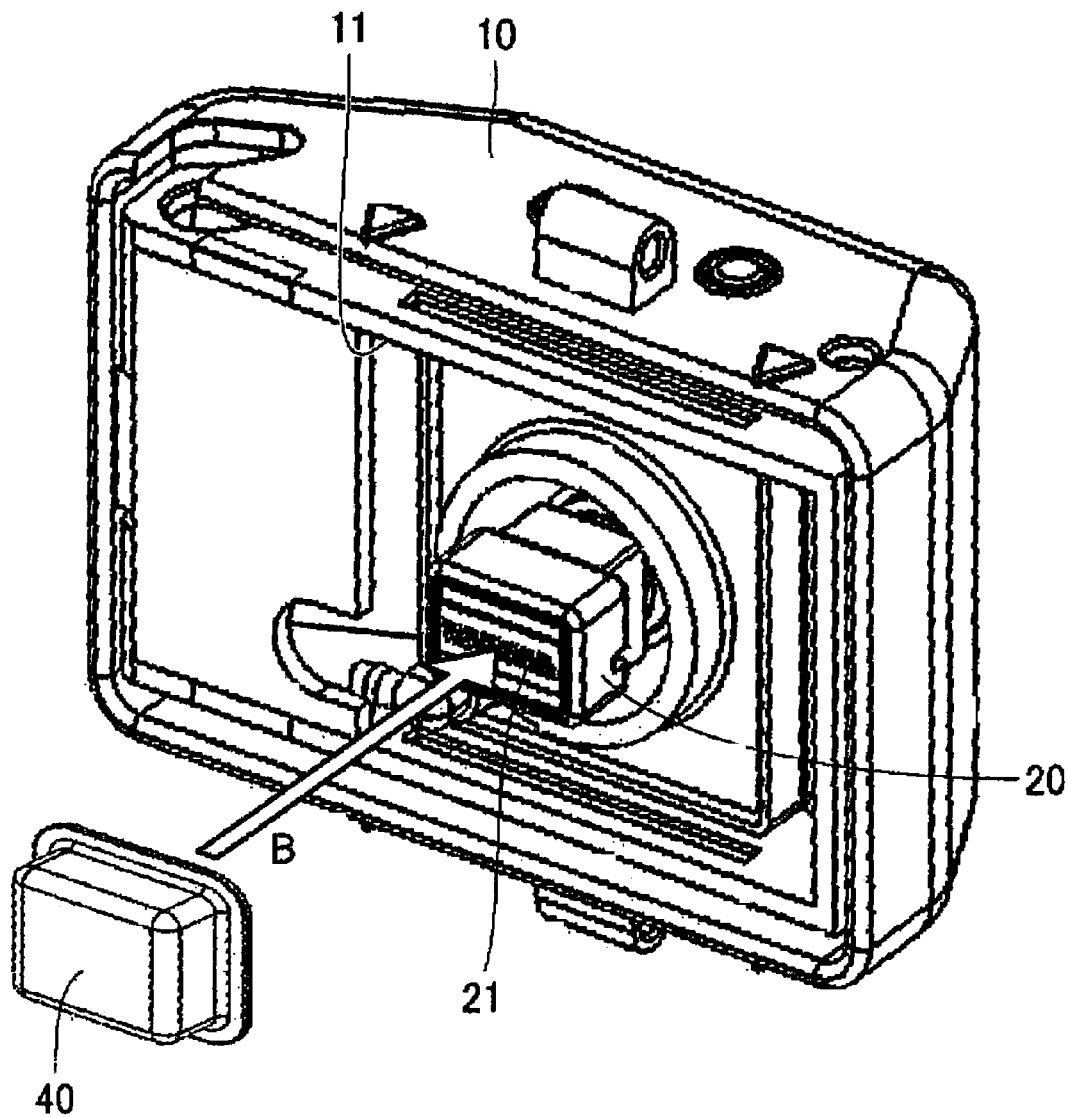
FIG. 4 shows a schematic perspective view of a pulse wave measuring apparatus, associated with the invention, and having been studied by the inventors.

FIG. 4 is a schematic perspective view showing a structure of a pulse wave measuring apparatus, associated with the invention, and having been studied by the inventors, in a concrete manner.

The pulse wave measuring apparatus includes, as shown in FIG. 4, mainly: a housing 10; a pressure sensing section 20; and a cap 40. The housing 10 is a member in a box-like shape and having an opening 11 at the bottom surface thereof, the pressure sensing section 20 is provided inside of the housing 10. The cap 40 can be freely mounted and demounted to the pressure sensing section 20. The cap 40 is mounted to the pressure sensing section 20 by a user in the non-measurement stage of the pulse wave measuring apparatus so as to cover the pressure sensing surface 21 of the pressure sensing section 20. Mounting of the cap 40 is implemented by fitting the cap 40 on the pressure sensing section 20 in a direction of an arrow mark B in the figure. In such a way, with the cap 40 provided, the pressure sensing surface 21 can be protected from an external force imposed on the pressure sensing surface 21 in the non-measurement stage.

In the pulse wave measuring apparatus with the structure, the apparatus is preferably constructed in a way such that in a state where the cap 40 is mounted, a predetermined gap is formed between the cap 40 and the pressure sensing surface 21. With such a construction, even in a case where an external force is imposed on the cap 40, it is avoided that the external force is transmitted directly to the pressure sensing surface 21 with the help of the cap; therefore, it is possible to protect the pressure sensing surface 21 with more of certainty.

In the structure, however, since a mounting operation of a cap is manually conducted by a user, there still remains a fear that when the cap is mounted to the pressure sensing section through the opening provided in the housing, the user injures the pressure sensing surface in error. Hence, though a possibility of injury on the pressure sensing surface is lower as compared with a conventional pulse wave measuring apparatus, protection of the pressure sensing surface is still insufficient.

In the structure, while the pressure sensing surface is protected by the cap, the pressure sensing section itself is not protected. Since the pressure sensing section is, as described above, mounted to the housing so as to be freely movable upwardly and downwardly relative to the housing, the pressure sensing section is in a state where the pressure sensing section protrudes downwardly inside of the housing even when the pressure sensing section is at a waiting position. Accordingly, a mounting strength of the pressure sensing section to the housing is not so high. Hence, in a case where an external force is imposed on the pressure sensing section in a lateral direction inside of the housing, there is a fear that the mounting portion of the pressure sensing section to the housing is broken. The cap of the above structure does no protect the pressure sensing section against an external force in the lateral direction. Hence, there still remains a fear that the pulse wave measuring apparatus is broken by an external force.

Therefore, the inventors studied on providing a protective mechanism protecting the pressure sensing section to the housing and have completed the invention. Detailed description will be given of embodiments of the invention with reference to the accompanying drawings.

(Embodiment 1)

A pulse wave measuring apparatus in a first embodiment of the invention is a pressurization type pulse wave measuring apparatus used in a way such that in a similar way to that in the pulse wave measuring apparatus associated with the invention on which the inventors studied, an opening provided in a housing is fixed so as to face a measuring site of a patient and the pressure sensing section mounted inside of the housing is pressed to the body surface through the opening to measure a pulse wave. Hence, in the figure, the same marks are attached to corresponding constituents similar to constituents of the pulse wave measuring apparatus and any of descriptions thereof is not repeated here.

Figure 5A:
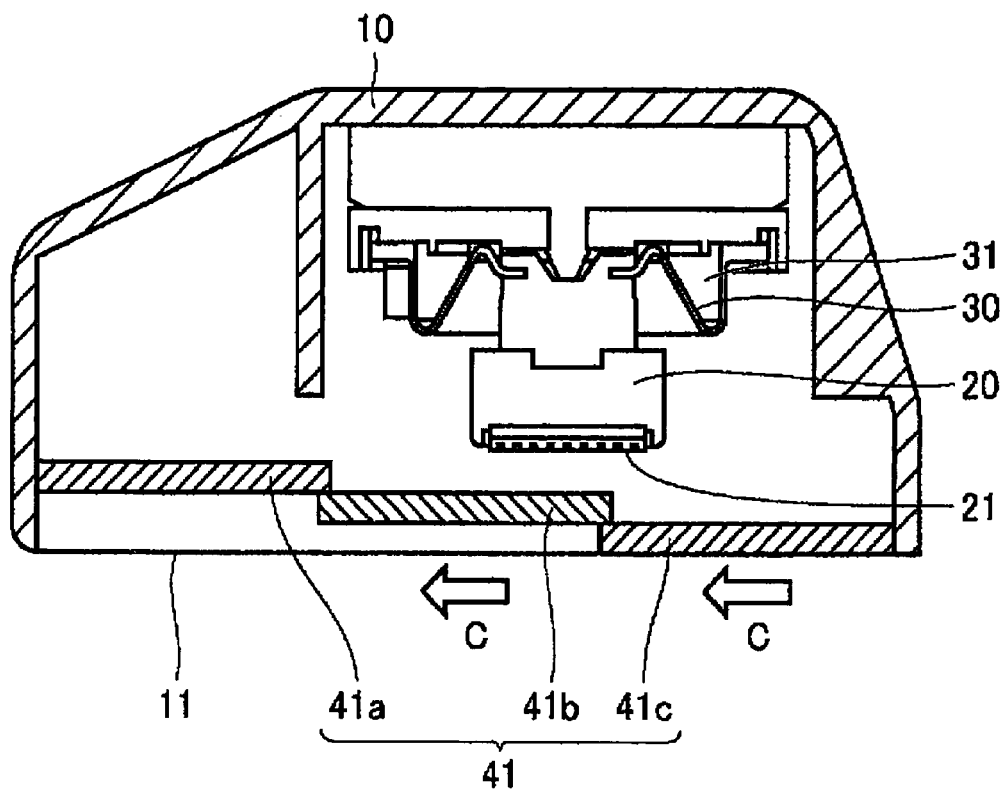
FIG. 5A shows a schematic sectional view of a structure of a protective mechanism of a pressure sensing section of a pulse wave measuring apparatus in a first embodiment of the invention in a state where a cover is closed and FIG. 5B shows a schematic sectional view of a structure of the protective mechanism in a state where the cover is opened.
Figure 5B:
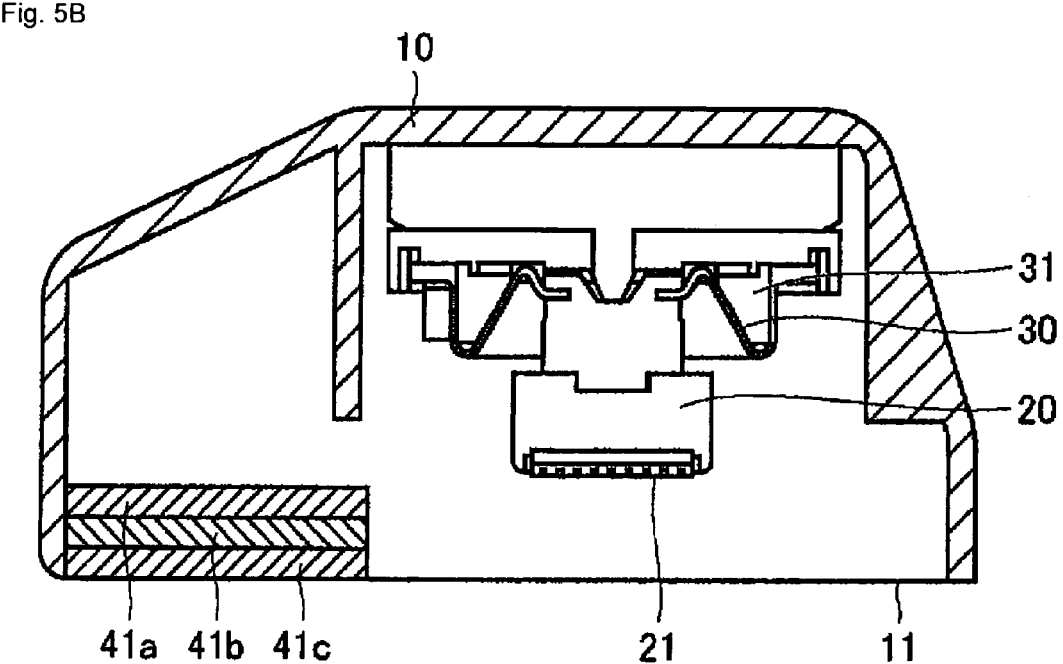

FIG. 5A is a schematic sectional view showing a structure of a protective mechanism of a pressure sensing section of a pulse wave measuring apparatus in an first embodiment of the invention in a state where a cover is closed and FIG. 5B is a schematic sectional view showing a structure of the protective mechanism in a state where the cover is opened.

The pulse wave measuring apparatus in this embodiment includes, as shown in FIG. 5A and FIG. 5B, mainly: a housing 10; and a pressure sensing section 20. The housing 10 is a member in a box-like shape having an opening 11 at the bottom surface thereof, and the pressure sensing section 20 is provided inside of the housing 10. An air bag 30 is attached in the top portion of the pressure sensing section 20. Inside of the air bag 30, it has an air room 31. The air bag 30 expands or contracts to thereby move the pressure sensing section 20 downwardly or upwardly.

The housing 10 is equipped with a slide cover 41 closing the opening 11 in a state where the pressure sensing section 20 is at a waiting position. The slide cover 41 is constituted of three plate members 41a to 41c combined, which are mounted to the housing 10 so as to be slidable along a groove (not shown) provided on the housing 10.

The plate members 41*b* and 41*c* are slid in a direction of an arrow mark C in the figure in use of the pulse wave measuring apparatus to thereby expose the pressure sensing surface 21 aligned, face to face, with the plane including the edge of the opening 11 of the housing 10 as shown in FIG. 5B. Such a construction enables a rising/falling operation of the pressure sensing section 20 for measuring a pulse wave. Note that an opening/closing operation of the slide cover 41 may be operated either manually or automatically.

With a construction adopted, equipped with the slide cover 41 that can freely opens and closes the opening 11 of the housing 10 as described above, it is possible to protect the pressure sensing surface 21 in the non-measurement stage. Furthermore, there is less of a fear that a use gets in touch with the pressure sensing surface 21 in error in an opening/closing operation of the slide cover 41, therefore enabling the pressure sensing surface 21 to be more surely protected. In this embodiment, since the slide cover 41 is mounted to the housing 10, a user cannot touches the pressure sensing section 20 in a state where the slide cover 41 is closed. Hence, no fear arises that an external force acts on not only the pressure sensing surface 21 but also the pressure sensing section 20, thereby enabling a pulse wave measuring apparatus hard to cause a trouble therein to be realized.

Figure 6A:
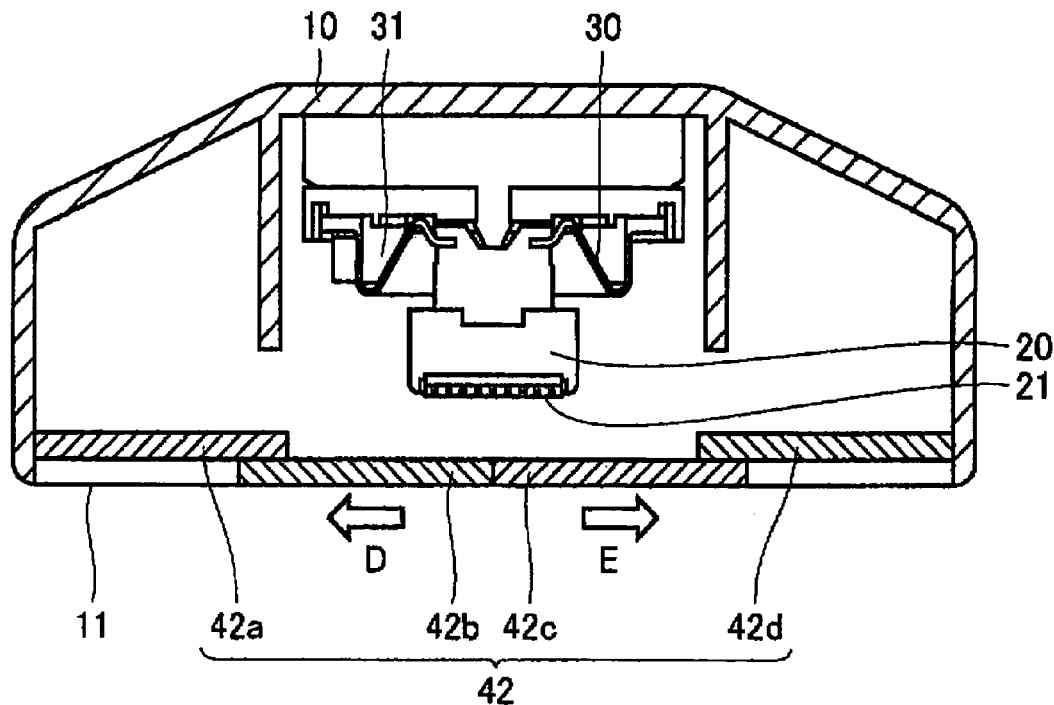
FIG. 6A shows a schematic sectional view of an example modification of the pulse wave measuring apparatus in the first embodiment of the invention in a state where a cover is closed and FIG. 6B shows a schematic sectional view of the example modification in a state where the cover is opened.
Figure 6B:
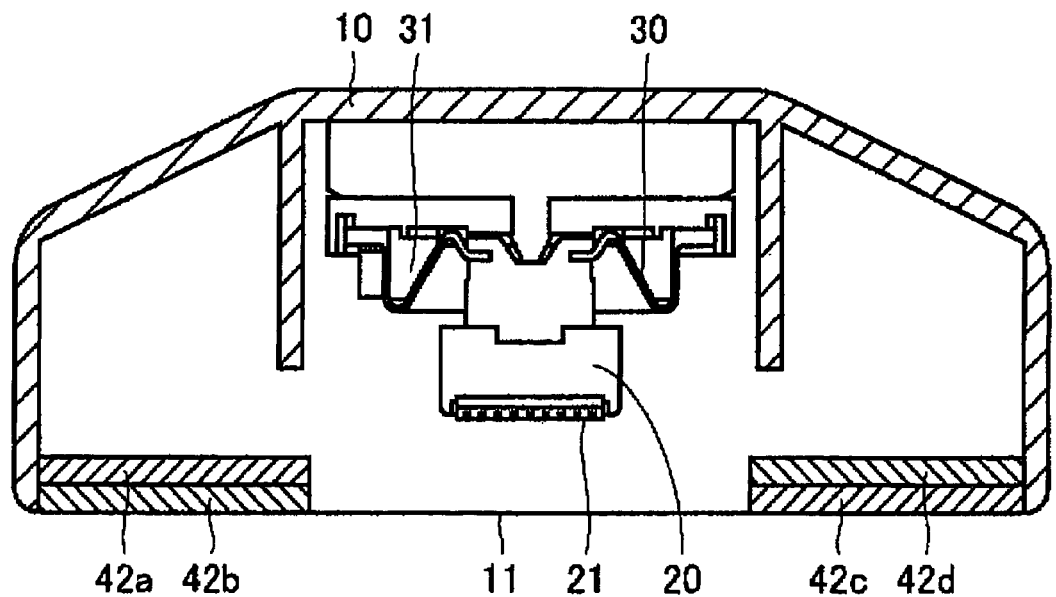

FIG. 6A is a schematic sectional view showing an example modification of the pulse wave measuring apparatus in this embodiment of the invention in a state where a cover is closed and FIG. 6B is a schematic sectional view showing the example modification in a state where the cover is opened. While in the above description, description is given showing a case where the slide cover is constituted of three plate members as an example, a pulse wave measuring apparatus shown in FIG. 6 shows a case where the slide cover is constituted of four plate members.

The housing 10 is, as shown in FIGS. 6A and 6B, equipped with a slide cover 42 closing an opening 11 in a state where a pressure sensing section 20 is at a waiting position. The slide cover 42 is constituted of four plate members 42*a* to 42*d* combined, which are mounted to the housing 10 so as to be slidable along a groove (not shown) provided on the housing 10.

The plate members 42*b* and 42*c* are slid in directions of arrow marks D and E, respectively, in the figure in use of the pulse wave measuring apparatus to thereby expose the pressure sensing surface 21 aligned, face to face, with the plane including the edge of the opening 11 of the housing 10 as shown in FIG. 6B. Such a construction adopted enables a rising/falling operation of the pressure sensing section 20 for measuring a pulse wave to be realized. Note that an opening/closing operation of the slide cover 42 may be conducted either manually or automatically.

In a case where the slide cover is used as the protective mechanism of the pressure sensing section in such a way, it is possible to adopt various kinds of structures.

In the pulse wave measuring apparatus adopting the slide cover as a protective cover as in this embodiment, a construction is preferable in which a distance between the slide cover and the pressure sensing surface in a state where the pressure sensing section is at the waiting position is more than a moving distance of the pressure sensing section moving between the waiting position and the measuring position. With such a construction adopted, even in a case where a user wrongly operates the pulse measuring apparatus to start a measuring operation in a state where the opening is kept to be closed by the protective cover, it is avoided for the pressure sensing surface to get in touch with the slide cover, thereby enabling the pressure sensing surface to be more surely protected.

(Embodiment 2)

A pulse wave measuring apparatus in the second embodiment of the invention is a pressurization type pulse wave measuring apparatus similar to that in the first embodiment. Hence, the same marks are attached to corresponding constituents similar to constituents of the first embodiment and any of descriptions thereof is not repeated here.

Figure 7A:
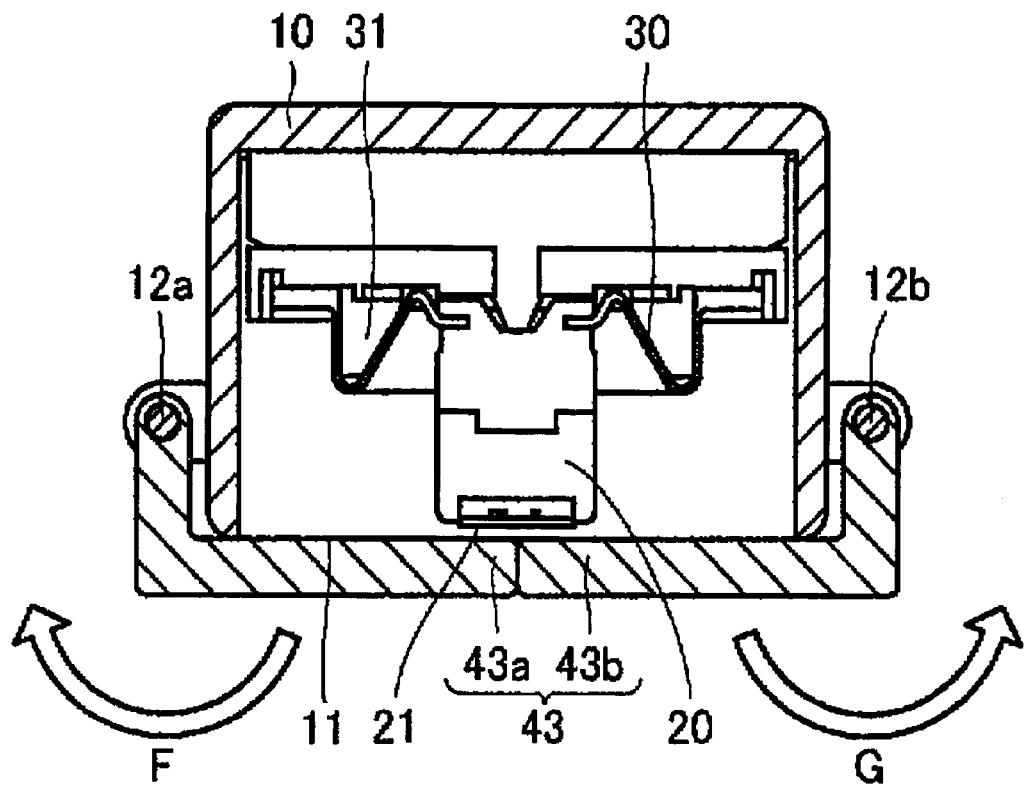
FIG. 7A shows a schematic sectional view of a structure of a protective mechanism of a pressure sensing section of a pulse wave measuring apparatus in a second embodiment of the invention when a cover is closed and FIG. 7B shows a schematic sectional view of the structure of the protective mechanism when the cover is opened.
Figure 7B:
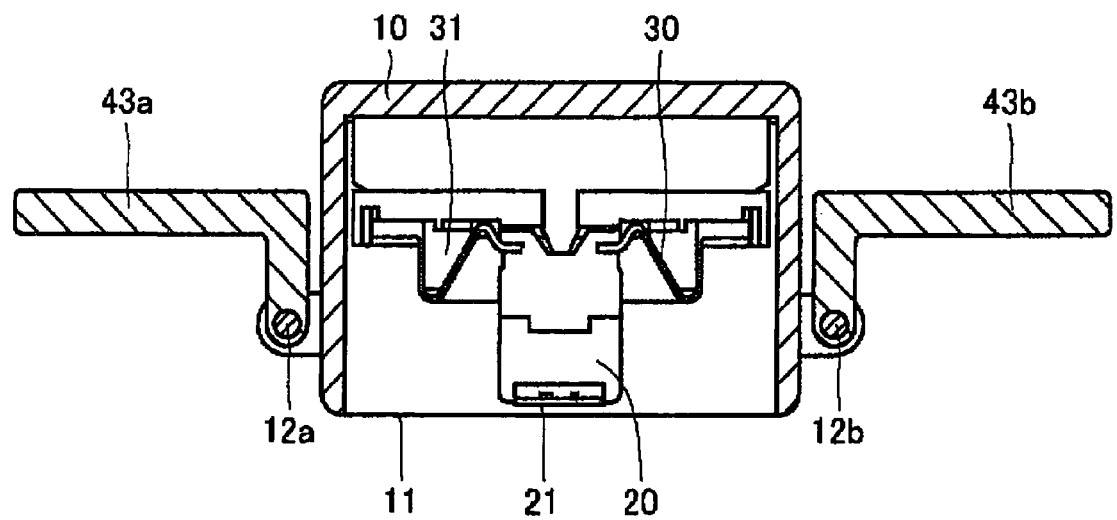

FIG. 7A is a schematic sectional view showing a structure of a protective mechanism of a pressure sensing section of a pulse wave measuring apparatus in a second embodiment of the invention when a cover is closed and FIG. 7B is a schematic sectional view showing the structure of a protective mechanism when the cover is opened.

The pulse wave measuring apparatus in this embodiment includes, as shown in FIGS. 7A and 7B, mainly: a housing 10; and a pressure sensing section 20. The housing 10 is a member in a box-like shape having a opening 11 at the bottom thereof and the pressure sensing section 20 is provided inside of the housing 10. The housing 10 is equipped with a pivotable cover 43 pivoting to close the opening 11 in a state where the pressure sensing section 20 is at a waiting position. The pivotable cover 43 is constituted of two members 43*a* and 43*b* in the sectional shape of a L letter combined, which are mounted to the housing 10 in a freely pivotable manner with pivots 12*a* and 12*b* attached to the housing 10.

The members 43*a* and 43*b* in the sectional shape of a L letter are pivoted in directions of arrows F and G, respectively, in the figure in the non-measurement stage of the pulse wave measuring apparatus to thereby expose the pressure sensing surface 21 aligned face to face with the plane including the edge of the opening 11 of the housing 10 as shown in FIG. 7B. Such a construction adopted enables a rising/falling operation of the pressure sensing section 20 for measuring a pulse wave. Note that an opening/closing operation of the pivotable cover 43 may be conducted either manually or automatically.

With a construction adopted, equipped with the pivotable cover 43 that can freely opens and closes the opening 11 of the housing 10 as described above, it is possible to protect the pressure sensing surface 21 in the non-measurement stage. Furthermore, there is less of a fear that a user gets in touch with the pressure sensing surface 21 in error in an opening/closing operation of the pivotable cover 43, therefore enabling the pressure sensing surface 21 to be more surely protected. In this embodiment, since the pivotable cover 43 is mounted to the housing 10, a user cannot touches the pressure sensing section 20 in a state where the pivotable cover 43 is closed. Hence, no fear arises that an external force acts on not only the pressure sensing surface 21 but also the pressure sensing section 20, thereby enabling a pulse wave measuring apparatus hard to cause a trouble therein to be realized.

FIG. 8A is a schematic sectional view showing an example modification of the pulse wave measuring apparatus in this embodiment when a pressure sensing section is located at a waiting position and FIG. 8B is a schematic sectional view showing the example modification when the pressure sensing section is located at a measuring position. While in FIG. 7, description is given of the pulse wave measuring apparatus in which a pivotable cover gets in touch with the peripheral brim of the opening in a state where the opening is closed by the pivotable cover as an example, in FIGS. 8A and 8B, there is shown the pulse wave measuring apparatus in which a slight clearance is left so that the pivotable cover does not get in touch with the peripheral brim in a state where the opening is closed by the pivotable cover.

In the pulse wave measuring apparatus shown in FIGS. 8A and 8B, a construction is adopted in which a distance L1 between the pivotable cover 43 and the pressure sensing surface 21 in a state where the pressure sensing section 20 is located at the waiting position is more than a moving distance D1 of the pressure sensing section 21 moving between the waiting position and the measuring position. With such a construction adopted, even in a case where a user wrongly operates the pulse measuring apparatus to start a measuring operation in a state where the opening 11 is kept to be closed by the pivotable cover 43, it is avoided for the pressure sensing surface 21 to get in touch with the pivotable cover 43, thereby enabling the pressure sensing surface 21 to be more surely protected.

Figure 9:
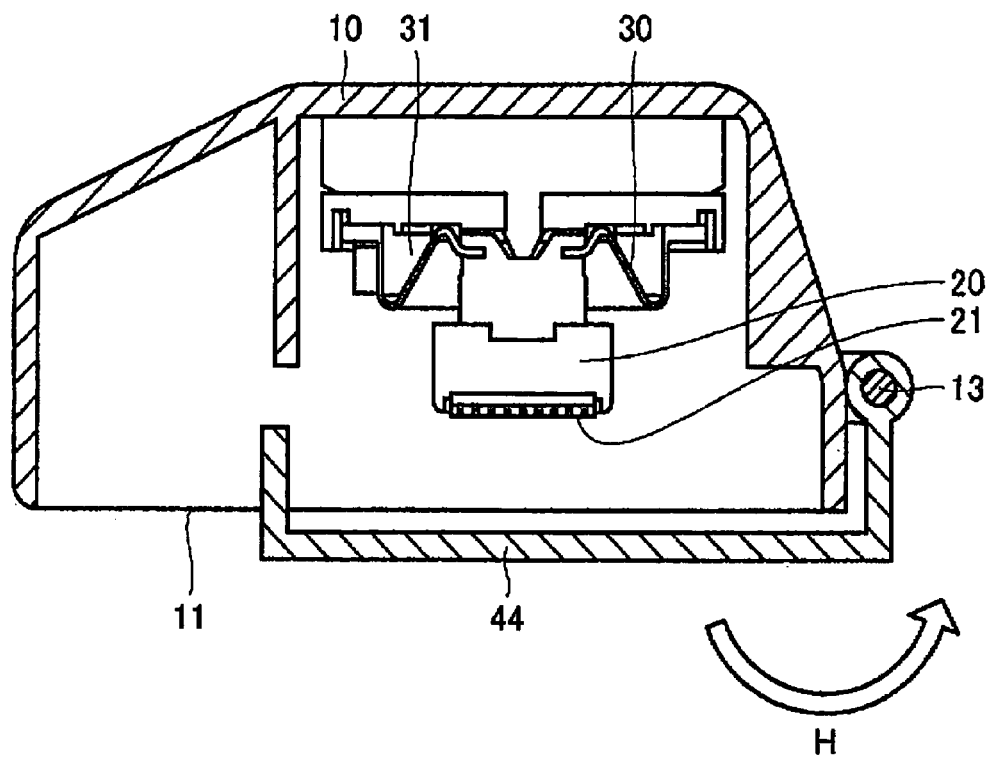
FIG. 9 shows a schematic sectional view of another example modification of the pulse wave measuring apparatus in the second embodiment of the invention.

FIG. 9 is a schematic sectional view showing another example modification of the pulse wave measuring apparatus in this embodiment of the invention. While in the above description, a case is exemplified where the pivotable cover is constituted of a pair of members in the sectional shape of a L letter, in the pulse wave measuring apparatus shown in FIG. 9, there is shown a construction in which the pivotable cover is a single member.

The housing 10 is, as shown in FIG. 9, equipped with a pivotable cover 44 closing the opening 11 in a state where the pressure sensing section 20 is in a waiting position. The pivotable cover 44 is a single member in the sectional shape of a L letter, which is mounted to the housing 10 with a pivot 13 attached to the housing 10 in a freely pivotable manner.

In use of the pulse wave measuring apparatus, the pivotable cover 44 is pivoted in a direction of an arrow mark H in the figure to thereby expose the pressure sensing surface 21 aligned, face to face, with the plane including the edge of the opening 11 of the housing 10. Such a state enables a rising/falling operation of the pressure sensing section 20 for measuring a pulse wave. With such a construction adopted, an opening/closing operation of the pivotable cover 44 may be conducted either manually or automatically.

In a case where a pivotable cover is used as a protective mechanism of the pressure sensing section in such a way, it is possible to adopt various kinds of other structures.

(Embodiment 3)

A pulse wave measuring apparatus in the third embodiment of the invention is a pressurization type pulse wave measuring apparatus similar to those in the first and second embodiments. Hence, the same marks are attached to corresponding constituents similar to constituents of the first and second embodiments and any of descriptions thereof is not repeated here.

Figure 10:
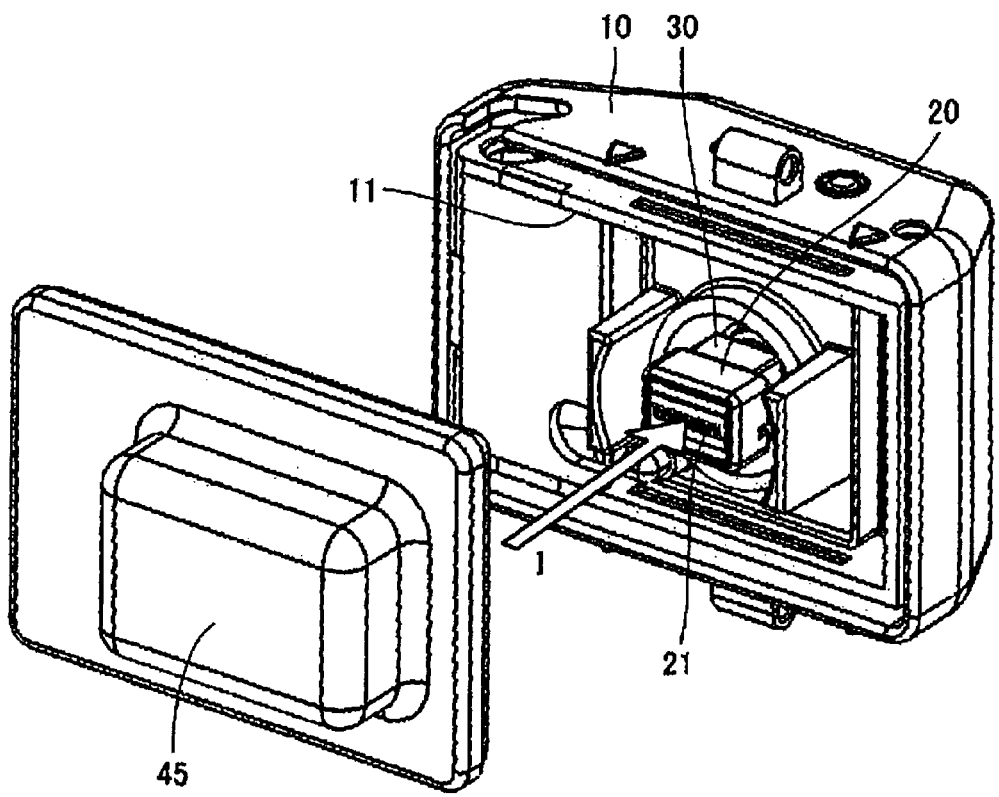
FIG. 10 shows a schematic perspective view of a structure of a protective mechanism of a pressure sensing section of a pulse wave measuring apparatus in the third embodiment of the invention.

FIG. 10 is a schematic perspective view showing a structure of a protective mechanism of a pressure sensing section of a pulse wave measuring apparatus in the third embodiment of the invention.

The pulse wave measuring apparatus in this embodiment includes, as shown in FIG. 10, mainly: a housing 10; and a pressure sensing section 20. The housing 10 is a member in a box-like shape having the opening 11 at the bottom surface thereof and the pressure sensing section 20 is provided inside of the housing 10. The housing 10 is equipped with a cap 45, which serves as a protective cover that freely opens and closes the opening 11. The cap 45 is mounted to the housing 10 by a user in the non-measurement stage of the pulse wave measuring apparatus so as to cover the pressure sensing surface 21 of the pressure sensing section 20. Mounting of the cap 45 is implemented by fitting the cap 45 onto the housing 10 in a direction of an arrow mark I.

With a construction adopted, equipped with the cap 45 that can freely opens and closes the opening 11 of the housing 10 and which is freely attachable and detachable to the housing 10 as described above, it is possible to protect the pressure sensing surface 21 in the non-measurement stage. Furthermore, there is less of a fear that a user gets in touch with the pressure sensing surface 21 in error in an attaching/detaching operation of the cap 45, therefore enabling the pressure sensing surface 21 to be more surely protected. In this embodiment, since the cap 45 is mounted to the housing 10, a user cannot touches the pressure sensing section 20 in a state where the cap 45 is closed. Hence, no fear arises that an external force acts on not only the pressure sensing surface 21 but also the pressure sensing section 20, thereby enabling a pulse wave measuring apparatus hard to cause a trouble therein to be realized.

FIG. 11A is a schematic sectional view of the pulse wave measuring apparatus in this embodiment of the invention when a pressure sensing section is located at a waiting position and FIG. 11B is a schematic sectional view of the pulse wave measuring apparatus when the pressure sensing section is located at a measuring position.

In the pulse wave measuring apparatus, as shown in FIGS. 11A and 11B, a construction is adopted in which a distance L2 between the cap 45 and the pressure sensing surface 21 in a state where the pressure sensing section 20 is located at a waiting position is more than a moving distance D2 of the pressure sensing section 20 moving between the waiting position and the measuring position. With such a construction adopted, even in a case where a user wrongly operates the pulse measuring apparatus to start a measuring operation in a state where the opening 11 is kept to be closed by the cap 45, it is avoided for the pressure sensing surface 21 to get in touch with the cap 45, thereby enabling the pressure sensing surface 21 to be more surely protected.

(Embodiment 4)

A pulse wave measuring apparatus in the fourth embodiment of the invention is a pressurization type pulse wave measuring apparatus similar to those in the first to third embodiments. Hence, the same marks are attached to corresponding constituents similar to constituents of the first to third embodiments and any of descriptions thereof is not repeated here.

Figure 12A:
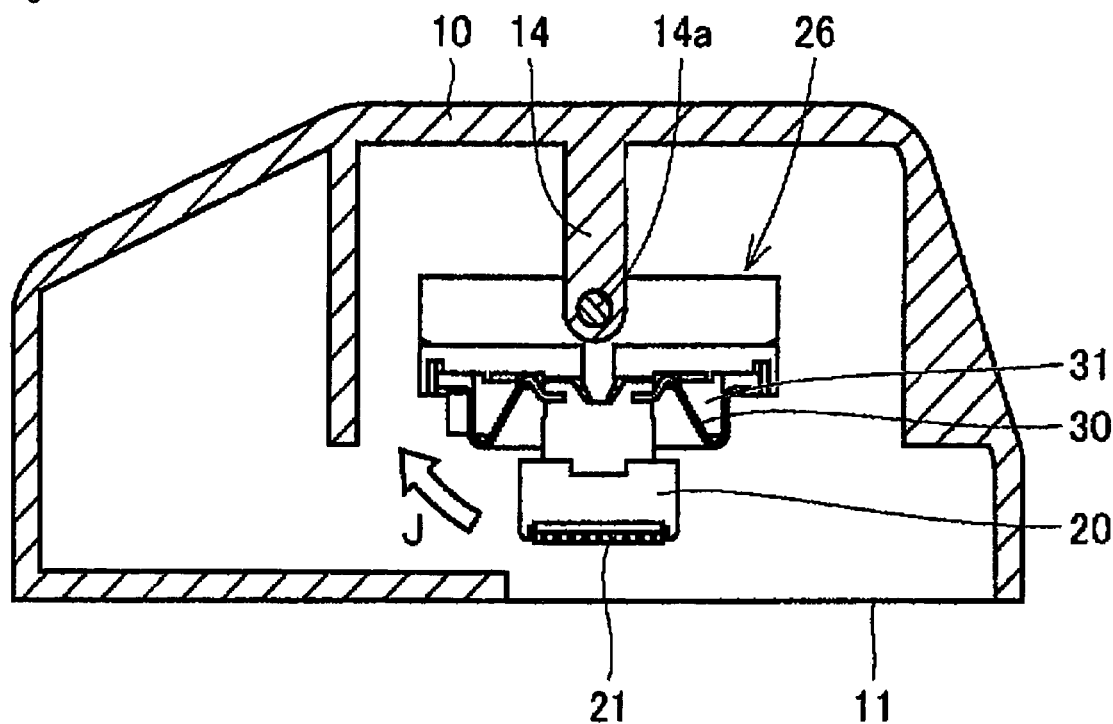
FIG. 12A shows a schematic sectional view of a structure of a protective mechanism of a pressure sensing section of a pulse wave measuring apparatus in a fourth embodiment of the invention when a pressure sensing surface is not protected and FIG. 12B shows a schematic sectional view of the structure of a protective mechanism when a pressure sensing surface is protected.
Figure 12B:
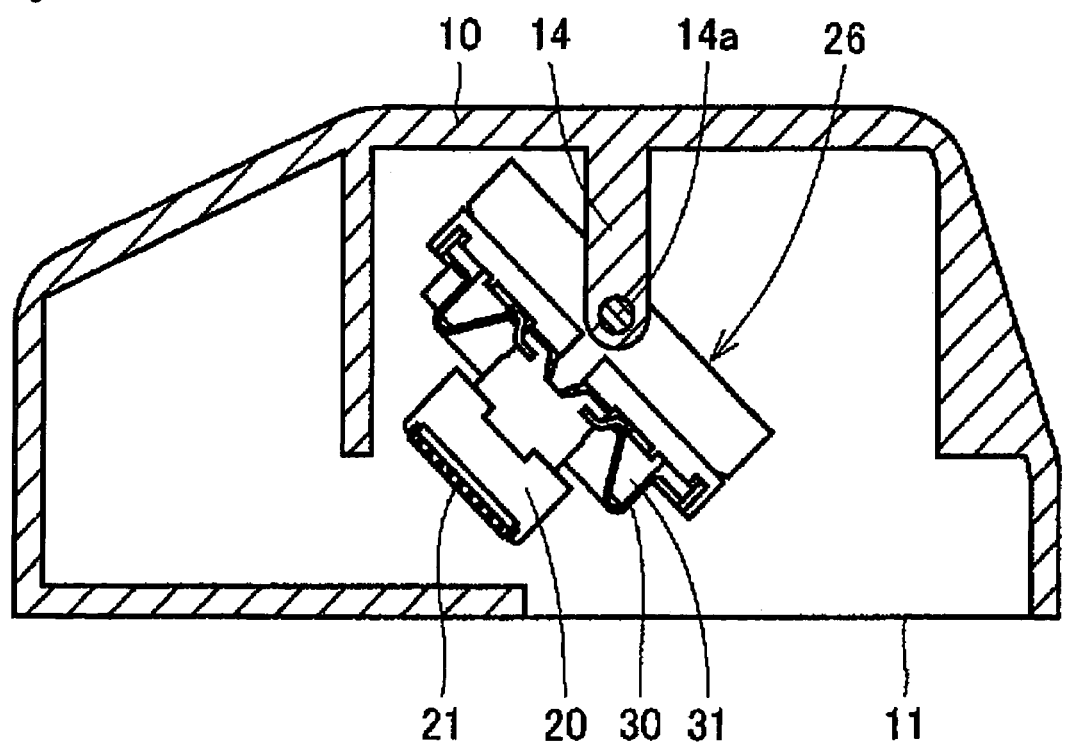

FIG. 12A is a schematic sectional view showing a structure of a protective mechanism of a pressure sensing section of a pulse wave measuring apparatus in a fourth embodiment of the invention when a pressure sensing surface is not protected and FIG. 12B is a schematic sectional view showing the structure of a protective mechanism when a pressure sensing surface is protected.

The pulse wave measuring apparatus in this embodiment includes, as shown in FIGS. 12A and 12B, mainly: a housing 10; and a pressure sensing section 20. The housing 10 is a member in a box-like shape having the opening 11 at the bottom surface thereof and the pressure sensing section 20 is provided inside of the housing 10. A support section 14 is provided at a predetermined position inside of the housing 10. A rotary shaft 14a is provided to a predetermined position of a pressure sensing unit 26 including the pressure sensing section 20. A rotating means is constituted of the support section 14 and the rotary shaft 14a. That is, the rotary shaft 14 of the pressure unit 26 is supported by the support section 14 of the housing 10 and thereby the pressure sensing unit 26 is mounted to the housing 10 in a freely rotatable manner. Note that a fixing means (not shown) is provided to the housing 10 and the pressure sensing unit 26 can be fixed in a state where the pressure sensing unit 26 is rotated half way.

In the measurement stage, the pressure sensing unit 26 is, as shown in FIG. 12A, fixed to the housing 10 in a state the pressure sensing surface 21 is aligned face to face with the plane including the edge of the opening 11. Such a state enables a rising/falling operation of the pressure sensing section for measuring a pulse wave.

In the non-measurement stage, on the other hand, the pressure sensing unit 26 is rotated in a direction of an arrow mark J by an angle and thereafter fixed so that the pressure sensing surface 21 is inclined to the plane including the edge of the opening 11 of the housing 10 as shown in FIG. 12B. By doing so, the pressure sensing surface 21 is covered with the housing 10. Note that the rotating operation and fixing operation of the rotation fixing means may be conducted either manually or automatically.

With a construction adopted, equipped with the rotation fixing means rotating and fixing the pressure sensing section 20 so that the pressure sensing surface 21 is inclined to the plane including the edge of the opening 11, it is possible to protect the pressure sensing plane 21 with the housing 10 in the non-measurement stage. Thereby, it is possible to realize a pulse wave measuring apparatus hard to cause a trouble therein.

(Embodiment 5)

A pulse wave measuring apparatus in the fifth embodiment of the invention is a pressurization type pulse wave measuring apparatus similar to those in the first to fourth embodiments. Hence, the same marks are attached to corresponding constituents similar to constituents of the first to fourth embodiments and any of descriptions thereof is not repeated here.

Figure 13:
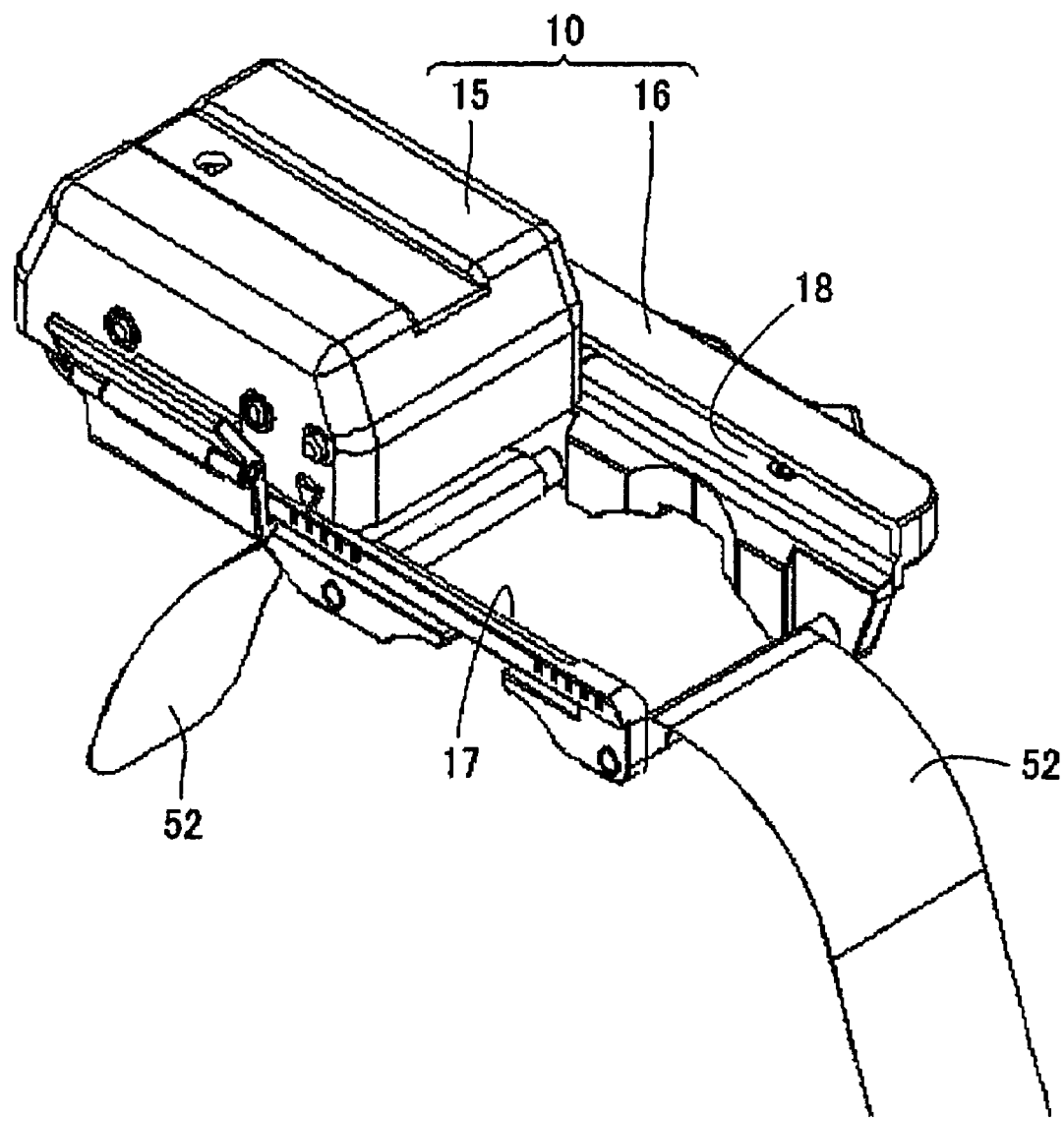
FIG. 13 shows a schematic perspective view of a structure of a pulse wave measuring apparatus in a fifth embodiment of the invention.
Figure 14A:
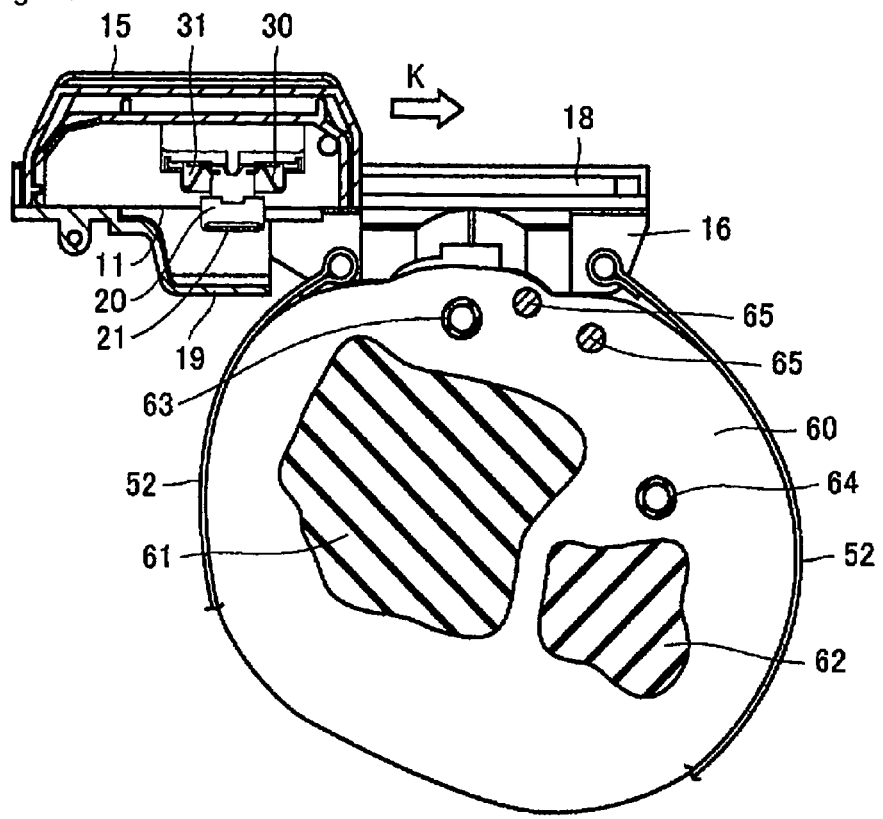
FIG. 14A shows a schematic sectional view of a pulse wave measuring apparatus in the fifth embodiment of the invention when the apparatus is set at a wrist of a patient in a state where a case body is located at a second position and FIG. 14B shows a schematic sectional view of the pulse wave measuring apparatus at the wrist of a patient in a state where the case body is located at a first position.
Figure 14B:
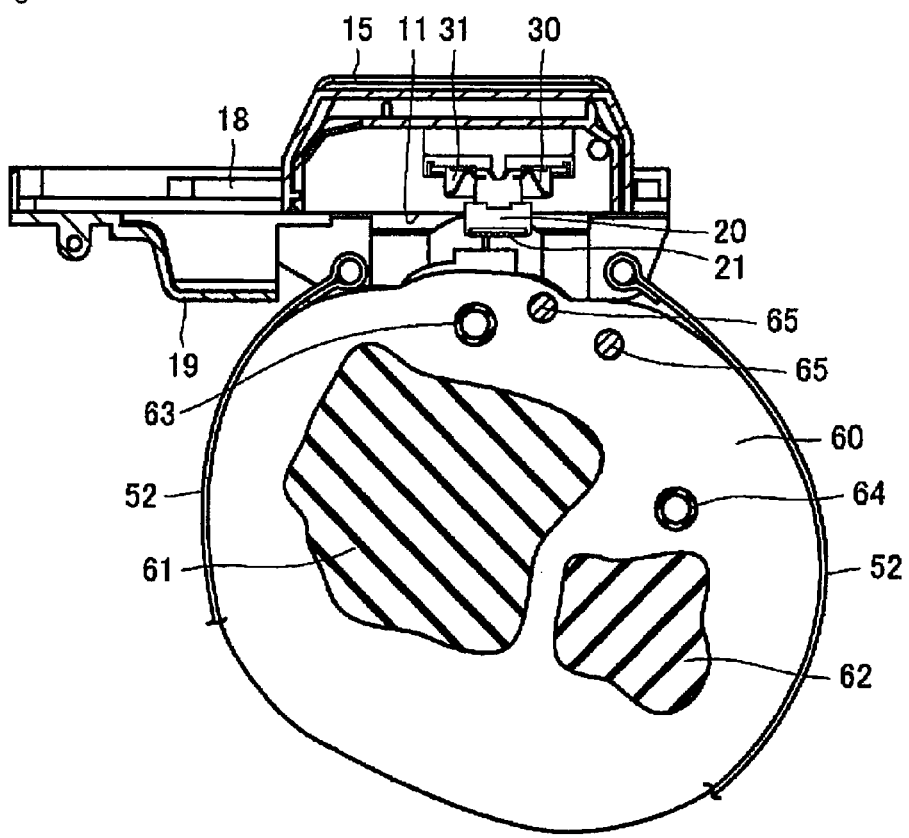

FIG. 13 is a schematic perspective view showing a structure of a pulse wave measuring apparatus in a fifth embodiment of the invention. FIG. 14A is a schematic sectional view of a pulse wave measuring apparatus in the fifth embodiment of the invention when the apparatus is set at a wrist of a patient in a state where a case body is located at a second position and FIG. 14B is a schematic sectional view of the pulse wave measuring apparatus at the wrist of patient in a state where the case body is located at a first position.

The pulse wave measuring apparatus in this embodiment, as shown in FIG. 13, is equipped with a case body 15 and a base body 16 as the housing 10. The case body 15 is a member in a box-like shape having the opening 11 (see FIG. 14) at the bottom surface thereof and the pressure sensing section 20 (see FIG. 14) including the pressure sensing surface 21 is provided inside of the case body 15. The base body 16 has an insertion hole 17 provided so that the pressure sensing section 20 can move upwardly and downwardly. A belt 52 is attached to a predetermined position of the base body 16. The base body 16 is a member for fixing the case body 15 to the human body.

With the construction in which the housing 10 is divided into the case body 15 and the base body 16 in such a way, it is facilitated to set the pressure sensing section 20 at a position on the body surface that is pressed with the pressure sensing section 20 (that is a position on the body surface right above an artery). That is, a user confirms a position on the body surface to be pressed with the pressure sensing section 20 by touch or the like, thereafter, the base body 16 is fixed on the body of a patient so that the position on the body surface to be pressed is located at the center of the insertion hole 17 of the base body 16 and then, the case body 15 is set on the insertion hole 17 of the base body 16, thereby enabling the pressure sensing section 20 to be set right above the artery with simplicity and convenience.

In the pulse wave measuring apparatus shown in FIG. 13, the case body 15 is mounted to the base body 16 so as to be movable by sliding thereon. To be concrete, the case body 15 is mounted to the base body 16 so as to movable by sliding along a groove 18 formed in the base body 16. The case body 15 is mounted to the base body 16 so that the pressure sensing surface 21 of the pressure sensing section 20 mounted to the case body 15 can move between a first position facing the insertion hole 17 provided in the base body 16 and a second position where the pressure sensing surface 21 does not face the insertion hole 17 as shown in FIG. 14A.

With such a construction adopted in which the case body 15 is mounted to the base body 16 so that the case body 15 can move by sliding relative to the base body 16, it is possible to realize a pulse wave measuring apparatus excellent in operability with a simple and convenient structure.

The pulse wave measuring apparatus in this embodiment has a protective cover section 19 at a predetermined position of the base body 16 as shown in FIGS. 14A and 14B. The protective cover section 19 is provided at a position at which the protective cover section 19 faces to the pressure sensing surface 21 in a state where the case body 15 is located at the second position. Since the case body 15 is located at the second position while in non-use, the pressure sensing surface 21 is protected by the protective cover section 19 (see FIG. 14A). Since in the measurement stage, the case body 15 is located at the first position, the pressure sensing section 20 can freely move upwardly and downwardly through the opening 11 of the case body 15 and using the insertion hole 17 of the base body 16 (see FIG. 14B). With such a construction adopted, the pressure sensing section 20 can move from the waiting position to the measuring position. Thereby, it is possible for the pressure sensing section 20 to move from the waiting position to the measuring position.

With such a construction adopted, the pressure sensing surface 21 can be protected with certainty by the protective cover section 19 provided in the base body in the non-measurement stage. Thereby, it is possible to realize a pulse wave measuring apparatus hard to cause a trouble therein with a simple and convenient structure.

FIG. 15A is a view showing a schematic sectional view of the pulse wave measuring apparatus in the fifth embodiment of the invention in a state where a pressure sensing section is located at a waiting position and FIG. 15B is a view showing a schematic sectional view of the pulse wave measuring apparatus in a state where the pressure sensing section is located at the measuring position.

In the pulse wave measuring apparatus in this embodiment, as shown in FIGS. 15A and 15B, a construction is adopted in which a distance L3 between the protective cover section 19 and the pressure sensing surface 21 in a state where the pressure sensing section 20 is located at the waiting position and the case body 15 is located at the second position is more than a moving distance D3 of the pressure sensing section 20 moving between the waiting position and the measuring position. With such a construction adopted, even in a case where a user wrongly operates the pulse wave measuring apparatus to start a measuring operation in a state where the case body 15 is kept to be located at the second position, it is avoided for the pressure sensing surface 21 to get in touch with the protective cover section 19, therefore, enabling the pressure sensing surface 21 to be more surely protected.

It should be understood that the embodiments disclosed above are presented by way of illustration but not by way of limitation in every respects. The technical scope of the invention is defined only by the terms of the appended claims and includes all alterations and modifications of the embodiments without departing from the technical scope and the equivalent thereof.

According to the invention, it is possible to realize a pulse wave measuring apparatus preventing breakage of a pressure sensing section including a pressure sensing surface in the non-measurement stage. Thereby, it is possible to provide a pulse wave measuring apparatus hard to cause a trouble therein.

What is claimed is:

1. A pulse wave measuring apparatus comprising:
   a housing having a protective cover, a case body having an opening, and a base body; and
   a pressure sensing section having a pressure sensing surface, mounted inside of the housing and moving freely upwardly and downwardly between a measuring position at which the pressure sensing surface is pressed to a human body to measure a pulse wave and a waiting position at which the pressure sensing section is accommodated inside of the housing,
   the protective cover protecting the pressure sensing section in a state where the pressure sensing section is located at the waiting position, wherein
   the case body accommodates the pressure sensing section and the base body is adapted to fix the case body to a human body,
   the base body has an insertion hole to accommodate the pressure sensing section moving between the waiting position and the measuring position in a freely, upwardly and downwardly movable manner,
   the case body is mounted to the base body so that the case body can slide along the base body between a first position at which the pressure sensing surface faces the insertion hole and a second position at which the pressure sensing surface does not face the insertion hole, and
   the protective cover faces the pressure sensing surface in a state where the case body is located at the second position.

2. The pulse wave measuring apparatus according to claim 1, wherein the pressure sensing section is located at the waiting position and a distance between the protective cover and the pressure sensing surface in a state where the case body is located at the second position is more than a moving distance of the pressure sensing section moving between the waiting position and the measuring position.

* * * * *